United States Patent [19]
Eibl et al.

[11] Patent Number: 5,830,467
[45] Date of Patent: Nov. 3, 1998

[54] PHARMACEUTICAL PREPARATION CONTAINING PROTEIN C AND A THROMBOLYTICALLY ACTIVE SUBSTANCE

[75] Inventors: Johann Eibl, Vienna; Anton Philapitsch, Ebenfurt; Hans Peter Schwarz, Vienna, all of Austria

[73] Assignee: Immuno Aktiengesellschaft, Vienna, Austria

[21] Appl. No.: 456,684

[22] Filed: Jun. 1, 1995

Related U.S. Application Data

[63] Continuation of Ser. No. 899,866, Jun. 17, 1992.

[30] Foreign Application Priority Data

Jun. 20, 1991 [AT] Austria ................................ 1240/91

[51] Int. Cl.$^6$ .............................. A61K 38/48; C12N 9/48; C12N 9/70; C12N 9/72
[52] U.S. Cl. .................................. 424/94.64; 424/94.63; 435/212; 435/214; 435/215; 435/216; 530/380; 530/381; 514/822; 514/834
[58] Field of Search ..................................... 435/212, 214, 435/215, 216; 424/94.64, 94.63; 530/380; 514/822, 834

[56] References Cited

U.S. PATENT DOCUMENTS 5,084,274  1/1992  Griffin et al. ....................... 424/94.64

FOREIGN PATENT DOCUMENTS

| B-39961/89 | 2/1990 | Australia . |
| B-30329/89 | 8/1992 | Australia . |
| 0 215 548 | 3/1987 | European Pat. Off. . |
| 0 287 028 | 10/1988 | European Pat. Off. . |
| 0 307 847 | 3/1989 | European Pat. Off. . |
| 0 318 201 | 5/1989 | European Pat. Off. . |
| 0 326 014 | 8/1989 | European Pat. Off. . |

OTHER PUBLICATIONS

Köhler et al., "Coninuous Cultures of Fused Cells Secreting Antibody of Predefined Specificity," *Nature*, vol. 256, pp. 495–497 (Aug. 1975).

Stassen et al., "Thrombolysis with Human Extrinsic (Tissue–Type) Plasminogen Activator in Rabbits with Experimental Jugular Vein Thrombosis," *J. Clin, Invest.*, vol. 71, pp. 368–376 (Feb. 1983).

Gruber et al., "Inhibition of Thrombus Formation by Infusion of Activated Protein C with Urokinase in a Primate Thrombosis Model," *Blood*, vol. 74, No. 7, Suppl. 1, Abstract No. 176 (Nov. 1989).

Yang et al., "Plasminogen, Alpha$_2$–antiplasmin, and Protein C Decline Following Infusions of Recombinanat Tissue Plaminogen Activator," *Seminars in Thrombosis and Hemostasis*, vol. 16, No. 3, pp. 242–244 (1990).

Gulba et al., "Increased Thrombin Levels During Thrombolytic Therapy in Acute Myocardial Infarction," *Circulation*, vol. 83, No. 3, pp. 937–944 (Mar. 1991).

Eisenberg et al., "Differential Effects of Activation of Prothrombin by Streptokinase compared With Urokinase and Tissue–Type Plasminogen Activator", *Thrombosis Research*, vol. 50:707–717, (1988).

Okajima et al., "Effect of Protein C and Activated Protein C on Coagulation and Fibrinolysis in Normal Human Subjects", *Thrombosis and Haemostasis*, vol. 63:48–53, (1990).

Vukovich et al., Replacement Therapy for a Homozygous Protein C Deficiency–State using a Concentrate of Human Protein C and S, British Journal of Haematology, vol. 70, 435–440, 1988.

Sigma Catalog, Sigma Chemical Company, p. 853, 1990.

Seligsohn et al., Homozygous Protein C Deficiency Manifested By Venous Thrombosis in the Newborn. N Engl. J. Med, 310:559–562, 1984.

Juhan–Vague et al., Plasma Levels of a Specific Inhibitor of Tissue–Type Plasminogen Activator (and Urokinase) in Normal and Pathological Conditions. Thromb. Res. 33:523–530, 1984.

*Primary Examiner*—Irene Marx
*Assistant Examiner*—Janet M. Kerr
*Attorney, Agent, or Firm*—Foley & Lardner

[57] ABSTRACT

A pharmaceutical preparation contains protein C and a thrombolytically active substance that does not activate protein C. This preparation prevents reocclusion usually occurring in the course of thrombolysis therapy.

8 Claims, 1 Drawing Sheet

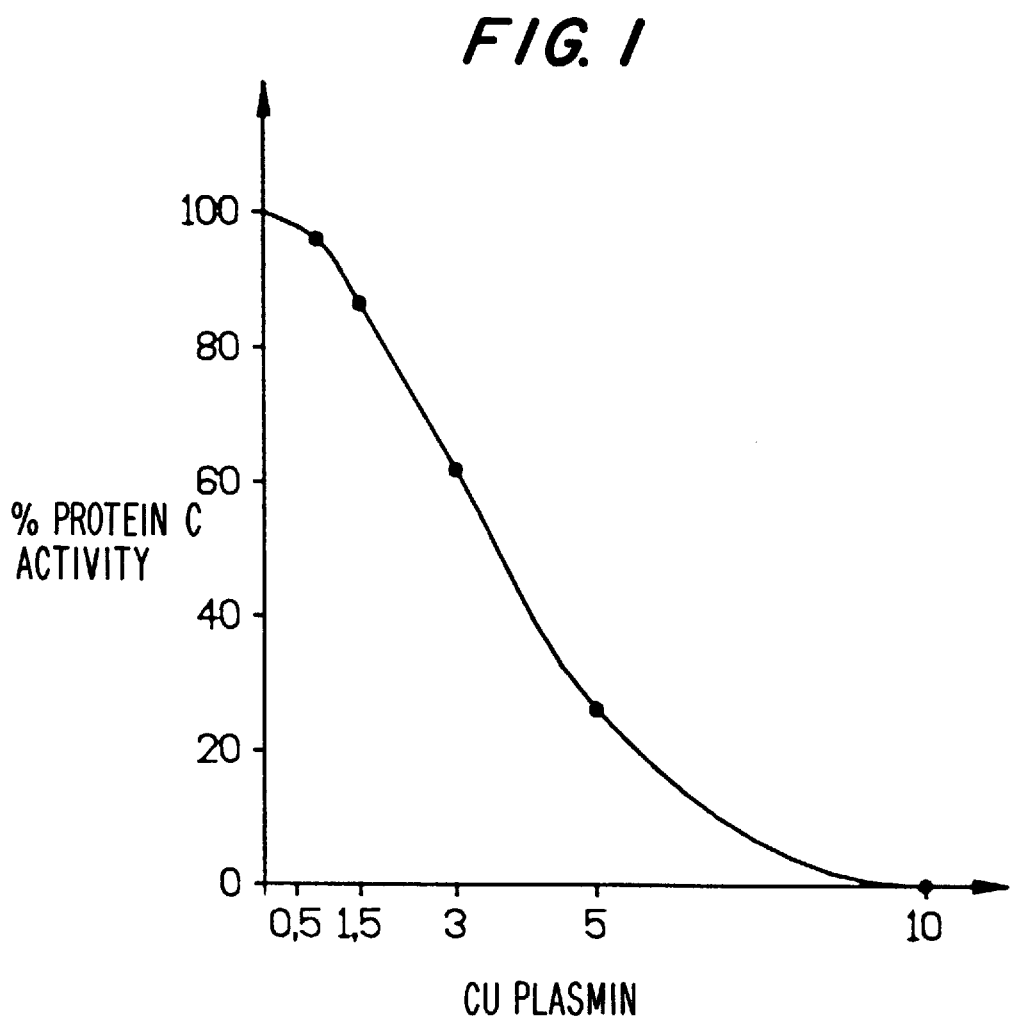

PHARMACEUTICAL PREPARATION CONTAINING PROTEIN C AND A THROMBOLYTICALLY ACTIVE SUBSTANCE

This application is a continuation, of application Ser. No. 07/899,866, filed Jun. 17, 1992.

The invention relates to a pharmaceutical preparation containing protein C.

BACKGROUND OF THE INVENTION

Many surgical procedures increase the risk of venous and arterial thromboses and of thromboembolism. Arterial and venous thromboses also may be caused by diseases. However, antithrombotic and thrombolytic therapies involve undesired side effects, such as bleeding or reocclusion.

The thrombolytic activity of substances, such as t-PA, urokinase, streptokinase or plasminogen, is based on the release of plasmin, which enables the dissolution of thrombi. At the same time, it is observed that thrombin is generated when administering thrombolytically active substances. The thrombin generation and subsequent reocclusion are presumed to be a generally undesired side effect of successful thrombolysis (Circulation 83, 937–944, (1991)).

In addition to an elevated thrombin activity, a change of the protein C concentration in blood is observed in thrombolysis patients (Seminars in Thrombosis and Hemostasis 16, 242–244 (1990)). Therapy is effected either with t-PA or with heparin or with a combination of t-PA and heparin. A reduction of the protein C concentration is observed only when administering t-PA-containing preparations. The direct degradation of protein C by t-PA or plasmin has not been considered, however.

In connection with undesired side effects of thrombolysis, it is suggested in EP-A - 0 318 201 to use activated protein C (aPC) alone or in combination with a thrombolytic agent to prevent acute arterial thrombotic occlusions, thromboembolism or stenosis. aPC is known to be an anticoagulatively effective enzyme, which, on the one hand, inhibits the formation of thrombin due to the proteolytic degradation of activated coagulation factor V and activated coagulation factor VIII and, on the other hand, supports fibrinolysis. For this reason, the dose of thrombolytic agent may be reduced.

Likewise, it is suggested in Blood 74, Suppl. 1, 50a, Abstract 176 (1989) to use a combined preparation containg aPC and urokinase to prevent the formation of thrombi in order to reduce the thrombolytic or antithrombotic doses of urokinase and simultaneously combat bleeding complications occurring in thrombolysis therapies. However, the administration of activated protein C suffers the disadvantage that the tendency to bleeding is favored by the immediate anticoagulant effect of aPC.

SUMMARY OF THE INVENTION

The invention has as its object to eliminate this disadvantage and to provide a pharmaceutical preparation that prevents reocclusion caused by an elevated thrombin activity after thrombolysis therapy has been carried out.

The preparation according to the invention contains protein C and a thrombolytically active substance that does not activate protein C.

It has been shown that the preparation according to the invention enables successful thrombolysis therapy without the risk of reocclusion.

Urokinase, tPA, Lys-plasminogen or streptokinase are particularly suitable as thrombolytically active substances.

Consequently, the invention also relates to the use of a thrombolytically active substance unable to activate protein C, in combination with protein C, to produce a drug for the treatment of thromboses and for the prevention of reocclusion.

The invention is based on the findings that plasmin generated by therapeutic thrombolytics not only degrades fibrin, but surprisingly also degrades protein C at the very high concentrations applied during thrombolysis therapy, thus provoking protein C deficiency and inducing hypercoagulability. This may be prevented by administering the thrombolytically active substance in combination with protein C or by administering protein C in the course of thrombolysis therapy, i.e., prior to, during and/or after thrombolysis therapy.

Preferably, protein C is contained in the preparation according to the invention at 10 to 50 U/mg protein. When ready for application, it should contain 90 to 450 U/ml. The content of thrombolytic agent in the preparation according to the invention appropriately is chosen so that usual amounts will be administered when applied.

The protein C-containing preparation according to the invention may be administered as an injection (30 to 80 U/kg) two or three times a day or as a continuous infusion (15 to 30 U/kg/h).

The invention will be described in more detail in the following.

BRIEF DESCRIPTION OF THE FIGURE

FIG. 1 depicts the degradation of Protein C by Plasmin.

DETAILED DESCRIPTION OF THE INVENTION

Preparation of Protein C

Highly pure protein C was recovered from a crude protein C fraction obtained from commercially available prothrombin complex concentrate. Purification was effected by affinity chromatography by means of monoclonal antibodies. Monoclonal anti-protein C antibodies were produced as follows:

BALB/C mice were immunized with 100 µg human protein C by intraperitoneal injection at two-week intervals. After six weeks, another 50 µg of human protein C was injected and fusion was carried out three days later. The myeloma cell line (P3-X-63-AG8-653, $1.5 \times 10^7$ cells) was mixed with $1.7 \times 10^8$ mouse spleen cells and fused according to the modified method of Köhler & Milstein by using PEG 1500 (Köhler G., Milstein C., Nature 256 (1975), 495–497).

Positive clones, assayed by means of ELISA, were subcloned twice. Ascites production was effected by injection of $5 \times 10^6$ hybridoma cells per BALB/C mouse two weeks after Pristan treatment.

The immunoglobulin was purified from ascites by means of ammonium sulfate precipitation and subsequent chromatography on QAE-Sephadex and, further, by chromatography on Sephadex G200. To reduce the risk of transmission of murine viruses, the antibody was subjected to a further virus inactivation step prior to immobilization. The monoclonal protein C antibodies thus obtained were coupled to CNBr-activated Sepharose 4B (Pharmacia). The following buffers were used for the purification of protein C by means of affinity chromatography:

Adsorption buffer: 20 mM Tris, 2 mM EDTA, 0.25M NaCl and 5 mM benzamidine;

Washing buffer: 20 mM Tris, 1M NaCl, 2 mM benzamidine, 2 mM EDTA, pH 7.4;

Elution buffer: 3M NaSCN, 20 mM Tris, 1M NaCl, 0.5 mM benzamidine, 2 mM EDTA.

In detail: The prothrombin complex concentrate was dissolved in the adsorption buffer, with approximately 10 g of the prothrombin complex concentrate being employed for a 20 ml monoclonal antibody column. Subsequently, the dissolved prothrombin complex concentrate was filtered, centrifuged at 20,000 r.p.m. for 15 min and sterilely filtered through a 0.8 μm filter. The sterilely filtered and dissolved prothrombin complex concentrate was applied to the column at a flow rate of 10 ml/h. Subsequently, the column was washed free of protein with the washing buffer, and finally the bound protein C was eluted by means of the elution buffer at a flow rate of 5 ml/h and the fractions were collected. The eluted protein C was dialyzed against a buffer (0.2 mol/l Tris, 0.15M glycine and 1 mM EDTA, pH 8.3). Protein C antigen concentration was determined using the method described by C. B. Laurell, *Scand. J. Clin. Lab. Invest.* 29, Suppl. 124:21–37 (1972), and protein C activity was determined using Protac activation.

The protein C eluate obtained was finished to a pharmaceutically applicable preparation in the following manner:

The eluate was first subjected to ultrafiltration and diafiltration steps. Diafiltration was carried out with a buffer containing 150 mmol NaCl and 15 mmol trisodium citrate.2H$_2$O per liter, at a pH of 7.4. The obtained filtrate was freeze-dried and virus inactivated by a one-hour vapor treatment at 80° C.±5° C. and at 1375±35 mbar.

The lyophilized, virus inactivated material was then dissolved in a sterile isotonic NaCl solution and potentially present antibodies or serum amyloid P were eliminated by means of ion exchange chromatography on Q-Sepharose. The purified solution was concentrated by means of an additional ultrafiltration and diafiltration step. After this step, 10 g albumin, 150 mmol NaCl and 15 mmol trisodium citrate per liter were added to the solution obtained. The pH of the solution was 7.5. Neither murine immunoglobulin nor factors II, VII, IX and X could be detected. Subsequently, the solution was sterilely filtered, filled in containers and lyophilized. The specific activity was 14 units protein C per mg of protein. One unit of protein C activity is defined as the protein C activity in 1 ml normal plasma and is calibrated against the first international standard of protein C. An amidolytic assay was used as the activity test, wherein protein C was activated by means of Protac (Pentapharm), a common protein C activator produced from a snake venom preparation.

Time-dependent degradation of protein C

Protein C was treated with plasmin and the degradation was observed by means of immunoblotting. To this end, 270 μl of a protein C-containing solution (8 μg/ml) were incubated with 270 μl plasmin (1 CU/ml) at 37° C. Accordingly, the substrate/enzyme ratio was 8:1 (μg/CU). After only 60 minutes, no protein C could be amidolytically detected any longer.

Dose-dependent degradation of protein C

In order to investigate the dose-dependent degradation of plasmatic protein C, 50 μl plasmin were each added to 50 μl human citrated plasma at concentrations of 10, 5, 3, 1.5 and 0.5 CU/ml, respectively. After a reaction time of 10 minutes, 50 μl antithrombin III-heparin complex (10 U ATIII, 50 U heparin per ml) were each added. By this addition, the reaction is stopped.

Protein C was amidolytically determined with the specific chromogenic substrate S 2366 (Kabi) upon activation with "PROTAC" (Pentapharm).

For comparison, plasmatic protein C without plasmin addition was treated in parallel. The results are apparent from the Figure (abscissa: CU plasmin; ordinate: % protein C activity). The Figure illustrates that protein C is completely degraded after only 10 minutes if a solution containing 10 CU/ml plasmin has been added.

What we claim is:

1. A pharmaceutical preparation for treating thrombosis and preventing reocclusion in a patient in need thereof, comprising protein C in zymogen form and a therapeutically effective amount of a thrombolytically active substance that does not activate protein C, wherein the protein C in zymogen form is present in a concentration that is effective to treat thrombosis and prevent reocclusion, and a pharmaceutically acceptable carrier.

2. The pharmaceutical preparation according to claim 1, wherein said thrombolytically active substance is selected from the group consisting of urokinase, tissue plasminogen activator, lys-plasminogen and streptokinase.

3. The pharmaceutical preparation according to claim 1, wherein the protein C in zymogen form is present in a concentration of about 90 to about 450 U/ml.

4. A method of treating thrombosis and preventing reocclusion in a patient, comprising administering to said patient protein C in zymogen form and a thrombolytically active substance that does not activate protein C, wherein the protein C in zymogen form is administered in a dosage of about 30 to about 80 units protein C in zymogen form per kilogram of body weight two to three times a day as an injection, or in a dosage of about 15 to about 30 units protein C in zymogen form per kilogram of body weight per hour as a continuous infusion.

5. The method according to claim 4, wherein said thrombolytically active substance is selected from the group consisting of urokinase, tissue plasminogen activator, lys-plasminogen and streptokinase.

6. A method of preventing reocclusion in a patient in thrombolysis therapy, comprising administering to said patient protein C in zymogen form prior to, during and/or after said thrombolysis therapy, wherein the protein C in zymogen form is administered in a dosage of about 30 to about 80 units protein C in zymogen form per kilogram of body weight two to three times a day as an injection, or in a dosage of about 15 to about 30 units protein C in zymogen form per kilogram of body weight per hour as a continuous infusion.

7. A method of producing a pharmaceutical preparation to treat thromboses and prevent reocclusion, comprising combining (i) protein C in zymogen form (ii) a therapeutically effective amount of a thrombolytically active substance that does not activate protein C in zymogen form and (iii) a pharmaceutically acceptable carrier to form the pharmaceutical preparation, wherein the pharmaceutical preparation contains the protein C in zymogen form in a concentration that is effective to treat thrombosis and prevent reocclusion.

8. The method of producing a pharmaceutical preparation according to claim 7, wherein the protein C in zymogen form is present in a concentration of about 90 to about 450 U/ml.

* * * * *